United States Patent [19]

Yates

[11] Patent Number: 4,906,796

[45] Date of Patent: Mar. 6, 1990

[54] PROCESS FOR PURIFYING 1,1,1,2-TETRAFLUOROETHANE

[75] Inventor: Stephen F. Yates, Arlington Heights, Ill.

[73] Assignee: Allied Signal Inc., Morris Township, Morris County, N.J.

[21] Appl. No.: 320,671

[22] Filed: Mar. 8, 1989

[51] Int. Cl.[4] .................... C07C 17/39; C07C 19/02
[52] U.S. Cl. ............................ 570/179; 570/134
[58] Field of Search ............................ 570/179

[56] References Cited

U.S. PATENT DOCUMENTS

| 3,215,747 | 11/1965 | Fainberg et al. | 570/179 |
| 3,804,910 | 4/1974 | Furrow | 570/179 |
| 3,819,493 | 6/1974 | Fozzard | 203/70 |
| 4,129,603 | 12/1978 | Bell | 260/653 |
| 4,158,675 | 6/1979 | Potter | 260/653.7 |
| 4,849,558 | 7/1989 | Goodman | 570/179 |

FOREIGN PATENT DOCUMENTS

| 3311751 | 10/1984 | Fed. Rep. of Germany | 570/179 |
| 846677 | 8/1960 | United Kingdom | 570/179 |

OTHER PUBLICATIONS

U.S. patent application No. 137,684, C. Chang et al.

Primary Examiner—J. E. Evans
Attorney, Agent, or Firm—Harold N. Wells; Jay P. Friedenson; Gerard P. Rooney

[57] ABSTRACT

R-1122 (2-chloro-1,1-difluoro-ethylene) can be substantially removed from a stream of R-134a over a zeolite or carbon molecular sieve having a mean pore size of about 3.8 to 4.8 Angstroms. Preferred are 5A synthetic zeolites or calcium chabazite.

9 Claims, No Drawings

PROCESS FOR PURIFYING 1,1,1,2-TETRAFLUOROETHANE

PRIOR ART

This invention relates to the purification of 1,1,1,2-tetrafluoroethane, also designated refrigerant 134a, which has been of particular interest as a replacement for chlorofluorocarbons having similar physical properties, particularly R-12. R-134a may be prepared by reaction of other fluorochlorocarbons with HF or alkali metal fluorides. Catalysts or electrochemical means may be employed to facilitate the reactions.

It is characteristic of such reactions that many by-products are formed, containing varying numbers of hydrogen, chlorine, and fluorine atoms on methane, ethane, and ethylene molecules. Some of these by-products are easy to separate by distillation, others are relatively harmless since their presence does not greatly alter the physical properties for which R-134a is useful. A by-product which must be removed because of its toxicity is 2-chloro-1,1-difluoro-ethylene (R-1122), although only relatively small amounts are typically present in R-134a as formed. R-1122 has a boiling point close to that of R-134a making them difficult to separate by distillation.

In U.S. Pat. No. 3,819,493 Fozzard discloses an extractive distillation process for separating 1,1-difluoroethane (R-152a) from R-134a produced by electrochemical fluorination of R-152a. The two compounds have a low relative volatility and saturated hydrocarbons having 4–10 carbon atoms are added to increase the relative volatility and facilitate their separation.

Bell in U.S. Pat. No. 4,129,603 removes R-1122 by contacting impure R-134a with an aqueous solution of a metal permanganate. The R-134a is derived from the reaction of HF with a haloethane such as 2-chloro-1,1,1-trifluoroethane over a chromium oxide or fluoride catalyst.

A different approach to removing R-1122 from R-134a is shown by Potter in U.S. Pat. No. 4,158,675. The reaction producing R-134a takes place at temperatures in the range of 325° to 375° C. in the presence of a chromium oxide or fluoride catalyst. Potter passes the effluent of the reaction into a second reactor containing a chromium catalyst but operated at 100° to 275° C. He shows that a substantial reduction of R-1122 is obtained.

Further improvement in methods of purifying R-134a, particularly with respect to eliminating R-1122 is desired and the present inventor has discovered a means for purification by adsorption which will be disclosed in detail below.

SUMMARY OF INVENTION

R-1122 (2-chloro-1,1-difluoro-ethylene) can be removed to below about 10 ppm by weight from a stream of R-134a (1,1,1,2-tetrafluoroethane) initially containing about 500 to 10,000 ppm by weight of R-1122 by passing the R-134a stream over a zeolite having a mean pore size between 3.8 and 4.8 Angstroms at a temperature of $-10°$ to $100°$ C. and a pressure of 100 to 860 kPa. With respect to the other impurities expected to be present in the R-134a stream, such zeolites have little or no capacity, making the removal of R-1122 highly selective. The preferred zeolites are 5A synthetic zeolite or calcium chabazite.

The process may be carried out with R-134a in the liquid or vapor phase. Where a fixed bed of zeolite particles is used, R-134a vapor may be passed over the particles with a gas hourly space velocity of 130 to 3600 $hr^{-1}$. The corresponding liquid space velocity for liquid phase operation would be 1 to 30 $hr^{-1}$.

The process also may be carried out with carbon molecular sieves rather than zeolites. The carbon molecular sieves should have a mean pore size of 3.8 to 4.8 Angstroms.

DESCRIPTION OF THE PREFERRED EMBODIMENTS

Background

Processes are under development which will produce R-134a, 1,1,1,2-tetrafluoroethane, a compound intended to replace R-12, which is believed to contribute to depletion of the ozone layer. Not only does the fluorination of a $C_2$ compound to produce R-134a require new catalysts and process conditions, but recovery and purification of R-134a must be considered. These latter steps will depend upon the by-products of the chemical reaction involved. The R-134a as it leaves the reactor in which it is produced will contain unreacted HF, HCl resulting from the removal of chlorine atoms from the feed compound, and various by-products containing hydrogen, chlorine, and fluorine atoms, as will be seen in the examples below. Of particular importance is 2-chloro-1,1-difluoro-ethylene (R-1122) which is toxic and must be removed from R-134a before use. Unfortunately, the boiling points of R-1122 and R-134a are quite close, $-17.1°$ C. and $-26.5°$ C. respectively, and they are not readily separated by distillation. The methods of the prior art discussed above have undesirable features and, consequently, the present inventor has sought and found an improved method, the selective adsorption of R-1122 in the presence of R-134a.

Adsorption of R-1122

It is, of course, preferred that a contaminant such as R-1122 be entirely removed selectively, not only from the principal compound in which it is found, i.e., R-134a, but also from other by-products which may be present. One skilled in the art will understand that such selective removal is uncommon. In most instances, an adsorbent has the ability to remove more than the target compound and thus the cost of removing the target compound increases and a secondary purification problem results when the adsorbent is regenerated. However, the present inventor has found that by selecting the proper molecular sieve nearly ideal separation of R-1122 from R-134a can be achieved.

The molecular sieves useful in the invention will have an average pore size in the range of about 3.8 to 4.8 Angstroms. Particularly useful are 5A synthetic zeolites and the naturally derived zeolite, calcium chabazite. The 5A zeolite has an average pore size of 4.3 Angstroms while the chabazite has an elliptical pore size of 3.7 by 4.2 Angstroms, which performs well as will be seen below, even though 4A zeolite (3.7 Å) does not. Thus, it is believed that the chabazite behaves as if it has an average pore size of about 3.9 Angstroms. These materials have silica to alumina mol ratios of about 1.0 to 4.0 and surface areas in the range of about 500 to 800 $m^2/gm$. As will be seen below, zeolites and other materials having a pore size differing from those described above have very different adsorptive properties and will not be capable of selectively adsorbing R-1122. The zeolites should be dried before use and this is preferably achieved by calcining at 400° C. under atmospheric pressure (or a lower temperature under vacuum) to provide a zeolite having a loss on ignition at 900° C. of less than 6% by weight.

In addition to zeolites, carbon molecular sieves have been found to be useful when their pore size is adjusted to the range given above. Carbon molecular sieves are derived from natural materials such as coal or from man-made polymers such as discussed in allowed U.S. patent application Ser. No. 137,684. These carbon molecular sieves are to be clearly distinguished from activated carbons, which are also derived from natural materials but have much larger pore sizes, up to about 30 Angstroms or more.

EXAMPLE 1

A 10 gm sample of the adsorbent to be tested was placed in a 9.5 mm diameter stainless steel tube and maintained at a temperature of 25° C. A synthetic mixture of gases expected to be present in partially purified R-134a was passed over the adsorbent sample at a rate of 60 mL/min and the composition of the effluent gases measured by gas chromatography using a 3048 mm long by 3.175 mm diameter column of 1% SP1000 on 60–80 mesh Carbopack B (Supelco Inc.) packing operated at 45° C. for 3 minutes and then programmed to increase at 8° C./min to 200° C. The results of a series of such tests are given in the following table.

TABLE A

| Component[1] | (wt) Feed (ppm) | 5A[2] | 4A[3] | AW-500[4] | Silicalite[5] | NaY[6] |
|---|---|---|---|---|---|---|
| $CO_2$ | 17 | 0 | 0 | 0 | 7 | 9 |
| R-143a | 662 | 761 | 718 | 689 | 270 | 704 |
| R-12 | 22 | 27 | 16 | 14 | 9 | 16 |
| R-1122 | 1034 | 0 | 1129 | 9 | 411 | 1073 |
| R-124 | 166 | 176 | 175 | 169 | 60 | 177 |
| R-133a | 4166 | 3472 | 4749 | 4400 | 0 | 4738 |
| R-114a | 88 | 100 | 97 | 91 | 28 | 94 |
| R-134a | remainder | | | | | |

[1]R-143a = $CH_3CF_3$ R-12 = $CCl_2F_2$ R-1122 = $CF_2$=CHCl R-124 = $CF_3CHClF$ R-133a = $CF_3CH_2Cl$ R-114a = $CF_3CCl_2F$ R-134a = $CF_3CH_2F$
[2]Supplied by UOP, average pore size 4.2 Å
[3]Supplied by UOP, average pore size 3.8 Å
[4]Calcium chabazite supplied by UOP, pore size 3.7 × 4.2 Å
[5]Supplied by UOP, average pore size 5.5 Å
[6]Supplied by UOP, average pore size 7.4 Å

Since the amount of the feed components was small relative to R-134a the absolute values of the components in the effluent should not be interpreted to be especially accurate, particularly when they are often larger than in the feed composition. R-134a represents about 99.5 wt. % of the gas and any adsorption of R-134a would tend to increase the fraction of the minor components in the effluent. This effect may account for many of the results. However, where significantly lower values are seen, it is believed that adsorption of that component has occurred. Where complete removal of a component is reported, that is believed to be a correct value.

Carbon dioxide, which could be derived from oxygen in the catalyst, was completely removed by 4A, 5A, and AW-500 zeolites.

R-143a, R-124, R-133a, R-12 and R-114a appear to be unaffected by the zeolites tested with the exception of silicalite, which removed a significant fraction of each component and clearly is non-selective.

The objective of the inventor was to selectively remove R-1122. It is apparent from the data above that two zeolites, 5A and AW-500, were capable of removing substantially all of the R-1122 with little or no capacity for the other components tested, except $CO_2$. The only other sample having an ability to remove R-1122 is silicalite, but only a fraction was removed. Consequently, it is concluded that zeolites having average pore size of about 3.8 to 4.8 Angstroms are required to reduce the R-1122 content of R-134a below about 10 ppm by weight.

EXAMPLE 2

The experiment of Example 1 was repeated using commercially available carbon molecular sieves and an activated carbon for comparison, with the following results:

TABLE B

| Component | Feed | PCB carbon[1] | HGR-805[2] | Kaldair[3] |
|---|---|---|---|---|
| $CO_2$ | 17 | 18 | 0 | 8 |
| R-143a | 662 | 685 | 613 | 427 |
| R-12 | 22 | 9 | 21 | 25 |
| R-1122 | 1034 | 0 | 4 | 852 |
| R-124 | 166 | 0 | 164 | 206 |
| R-133a | 4166 | 0 | 1566 | 6608 |
| R-114a | 88 | 0 | 91 | 109 |
| R-134a | remainder | — | — | — |

(1) Activated carbon supplied by Calgon Corp., average pore size 30 Å
(2) Supplied by Takeda Chemical Industries, average pore size 4.4 Å
(3) Supplied by Kaldair Inc., average pore size 3.5 Å

The PCB carbon is an activated carbon having a large pore size and is shown here for comparison. The activated carbon is capable of removing many of the components completely. In contrast, the Takeda carbon molecular sieve, which has an average pore size of 4.4 Angstroms shows a performance very similar to the zeolites (5A and AW-500) of Table A, each having the ability to selectively remove substantially all of the R-1122 while leaving the other components (excepting $CO_2$) in the R-134a stream. In contrast, the Kaldair carbon molecular sieve has a pore size too small to remove R-1122.

PROCESS

R-134a will be produced by catalytic hydrofluorination of a $C_2$ compound containing chlorine atoms, which are replaced during the process by fluorine atoms. Conversion to R-134a will be only partial and many by-products will be produced, along with HCl which is a major product of the reaction. Consequently, the reactor effluent will be separated by distillation to concentrate the R-134a product and to produce a recycle stream of unreacted feed. The resulting impure R-134a stream will contain unreacted HF, HCl, and minor amounts of various by-product impurities, including R-1122. The HF and HCl can be removed selectively by a technique disclosed by others and not part of the present invention. Once done, the R-134a will still contain impurities which should be removed, particularly R-1122, which is toxic and must be removed. The present process is intended to be selective for removal of R-1122 down to or below 10 ppm by weight from a concentrated R-134a stream from which HF and HCl have already been removed. If HF and HCl are present they would be expected to be adsorbed to some extent, but they would be expected also to attack zeolites, although a carbon molecular sieve might be used.

The R-134a feed stream could be either in the liquid or gas phase, although the liquid phase would be preferred to avoid the costs of vaporizing and later condensing the feed stream. Various techniques known to those skilled in the art could be used for contacting the R-134a stream with the molecular sieve adsorbent (zeolite or carbon), such as fluidized or moving beds, but typically a packed bed of adsorbent particles would be used. Selection of the particle size, bed shape, and the space velocity of the R-134a stream would be determined according to known principles as required to provide nearly complete removal of R-1122. Generally, the gas hourly space velocity of the R-134a stream would be about 130 to 3600 $hr^{-1}$ when operating with a vapor feed. The corresponding liquid space velocity would be 1 to 30 $hr^{-1}$. Adsorption would be carried out at a suitable temperature, generally between about $-10°$ C. to $100°$ C. and a pressure dependent upon whether liquid or vapor contacting is desired, between about 100 to 860 kPa. As indicated in the above examples it may be expected that R-1122 will be completely removed, leaving 10 ppm or less by weight in the R-134a stream ready for further purification if desired. The R-1122 will be separated when the adsorbent is regenerated and may be disposed of by various means.

The adsorbent bed should provide an optimum capacity for R-1122, balancing the costs for equipment and adsorbent versus the costs of regeneration. When the useful capacity has been reached, the adsorbent will be regenerated by heating the bed with a gas stream to desorb the R-1122. The R-134a remaining in the vessel and on the adsorbent will be removed first and recovered and then the regeneration process will be carried out. After the bed has been fully heated and the R-1122 removed, it will be cooled and reintroduced to service. The conditions needed to optimally regenerate the adsorbent will be determined by the adsorbent used and the available utilities. Typically, it would be expected that heating the bed of adsorbent to about $150°$ to $400°$ C. with a stream of nitrogen would provide satisfactory regeneration.

I claim:

1. A process for removing impurities from 1,1,1,2-tetrafluoroethane (R-134a) containing about 50–10,000 ppm by weight of 2-chloro-1,1-difluoro-ethylene (R-1122) comprising passing said 1,1,1,2-tetrafluoroethane over a zeolite having a mean pore size between 3.8 and 4.8 Angstroms at a temperature of $-10°$ to $100°$ C. and a pressure of 100 to 860 kPa and recovering 1,1,1,2-tetrafluoroethane containing less than 10 ppm by weight of 2-chloro-1,1-difluoro-ethylene.

2. The process of claim 1 wherein said zeolite is a 5A synthetic zeolite.

3. The process of claim 1 wherein said zeolite is calcium chabazite.

4. The process of claim 1 wherein said zeolite is a fixed bed of zeolite particles and the gas hourly space velocity of said 1,1,1,2-tetrafluoroethane is 130 to 3600 $hr^{-1}$.

5. The process of claim 1 wherein said zeolite is calcined to provide a loss on ignition at $900°$ C. of less than 6% by weight.

6. The process of claim 1 wherein said zeolite is a fixed bed of zeolite particles and the liquid hourly space velocity of said 1,1,1,2-tetrafluoroethane is 1 to 30 $hr^{-1}$.

7. A process for removing impurities from 1,1,1,2-tetrafluoroethane containing about 500–10000 ppm by weight of 2-chloro-1,1-difluoro-ethylene comprising passing said 1,1,1,2-tetrafluoroethane over a carbon molecular sieve having a mean pore size between 3.8 and 4.8 Angstroms at a temperature of $-10°$ to $100°$ C. and a pressure of 100 to 860 kPa and recovering 1,1,1,2-tetrafluoroethane containing less than 10 ppm by weight of 2-chloro-1,1-difluoro-ethylene.

8. The process of claim 7 wherein said carbon molecular sieve is a fixed bed of carbon particles and the gas hourly space velocity of said 1,1,1,2-tetrafluoroethane is 130 to 3600 $hr^{-1}$.

9. The process of claim 7 wherein said carbon molecular sieve is a fixed bed of carbon particles and the liquid hourly space velocity of said 1,1,1,2-tetrafluoroethane is 1 to 30 $hr^{-1}$.

* * * * *

UNITED STATES PATENT AND TRADEMARK OFFICE
CERTIFICATE OF CORRECTION

PATENT NO. : 4,906,796
DATED : March 6, 1990
INVENTOR(S) : Yates

It is certified that error appears in the above-identified patent and that said Letters Patent is hereby corrected as shown below:

Column 2, line 59: "(3.7 å)" should read --(3.7 Å)--.
Column 4, line 27: "30 å" should read --30 Å--;
          line 29: "4.4 å " should read --4.4 Å--;
          line 30: "3.5 å" should read --3.5 Å--.

Signed and Sealed this

Nineteenth Day of March, 1991

*Attest:*

HARRY F. MANBECK, JR.

*Attesting Officer*      *Commissioner of Patents and Trademarks*